(12) United States Patent
Riepl

(10) Patent No.: US 9,320,744 B2
(45) Date of Patent: Apr. 26, 2016

(54) DHEA BIOADHESIVE CONTROLLED RELEASE GEL

(71) Applicant: DHEA LLC, Bismarck, ND (US)

(72) Inventor: Michael S. Riepl, Bismarck, ND (US)

(73) Assignee: DHEA LLC, Bismarck, ND (US)

( * ) Notice: Subject to any disclaimer, the term of this patent is extended or adjusted under 35 U.S.C. 154(b) by 0 days.

(21) Appl. No.: 14/688,603

(22) Filed: Apr. 16, 2015

(65) Prior Publication Data

US 2015/0297510 A1 Oct. 22, 2015

Related U.S. Application Data

(63) Continuation of application No. 13/696,787, filed as application No. PCT/US2011/056819 on Oct. 19, 2011, now abandoned.

(51) Int. Cl.
| | |
|---|---|
| *A61K 31/5685* | (2006.01) |
| *A61K 9/00* | (2006.01) |
| *A61K 31/355* | (2006.01) |
| *A61K 9/06* | (2006.01) |
| *A61K 47/32* | (2006.01) |
| *A61K 31/00* | (2006.01) |
| *A61K 31/566* | (2006.01) |

(52) U.S. Cl.
CPC ........... *A61K 31/5685* (2013.01); *A61K 9/0034* (2013.01); *A61K 9/06* (2013.01); *A61K 31/00* (2013.01); *A61K 31/355* (2013.01); *A61K 47/32* (2013.01); *A61K 31/566* (2013.01)

(58) Field of Classification Search
None
See application file for complete search history.

(56) References Cited

U.S. PATENT DOCUMENTS

| 4,542,129 | A | | 9/1985 | Orentreich |
| 5,208,031 | A | * | 5/1993 | Kelly ............................ 424/412 |
| 5,814,341 | A | * | 9/1998 | Fankhauser et al. .......... 424/493 |
| 5,955,455 | A | | 9/1999 | Labrie |
| 6,294,550 | B1 | * | 9/2001 | Place et al. .................... 514/302 |
| 6,365,200 | B1 | * | 4/2002 | Birnholz ................ A61K 8/416 424/725 |
| 7,186,706 | B2 | | 3/2007 | Rosario-Jasin et al. |
| 7,563,565 | B1 | | 7/2009 | Matsuo et al. |
| 7,592,021 | B2 | | 9/2009 | Shankar et al. |
| 7,884,092 | B2 | | 2/2011 | Labrie |
| 2004/0044080 | A1 | | 3/2004 | Place et al. |
| 2005/0147581 | A1 | | 7/2005 | Zamiri et al. |
| 2005/0181057 | A1 | | 8/2005 | Rosenberg et al. |
| 2005/0281762 | A1 | * | 12/2005 | Modak ..................... A61K 8/27 424/59 |
| 2006/0018937 | A1 | | 1/2006 | Friedman et al. |
| 2006/0115532 | A1 | | 6/2006 | Shankar et al. |
| 2007/0270394 | A1 | | 11/2007 | El-Alfy et al. |
| 2008/0113031 | A1 | | 5/2008 | Moodley et al. |
| 2009/0124584 | A1 | | 5/2009 | Lyle |
| 2011/0091403 | A1 | | 4/2011 | Yu et al. |

FOREIGN PATENT DOCUMENTS

| WO | WO 97/03676 | 2/1997 |
| WO | WO 97/12618 | 4/1997 |
| WO | WO 2007/012977 | 2/2007 |

OTHER PUBLICATIONS

Loprinzi et al., "Phase III randomized double-blind study to evaluate the efficacy of a polycarbophil-based vaginal moisturizer in women with breast cancer", J. Clin. Oncology, 15(3), pp. 969-973 (1997) (abstract).*
Labrie et al., "Effect of intravaginal DHEA on serum DHEA and eleven of its metabolites in postmenopausal women", J. Ster. Biochem. & Mol. Bio., 111, pp. 178-194 (2008).*
Wedgwood Pharmacy, "Dehydroepiandrosterone (DHEA): Transdermal Gel", www.wedgwoodrx.com/items/dehydroepiandrosterone-dhea-transdermal-gel.html (2 sheets)(at least Jan. 24, 2011).

* cited by examiner

*Primary Examiner* — Bethany Barham
*Assistant Examiner* — Barbara Frazier
(74) *Attorney, Agent, or Firm* — Richard C. Litman

(57) ABSTRACT

The DHEA bioadhesive controlled release gel includes DHEA mixed in a polymeric gel for the purpose of treating atrophic vaginitis, vaginal dryness, dyspareunia, itching, burning, irritation, increase in pH and decreased vaginal flora. The gel adheres to vaginal tissue and protects the DHEA from systemic absorption, which prevents leakage, loss of DHEA, and elevated levels of systemic DHEA. The gel is configured to slowly erode over time so as to deliver a predetermined dose of DHEA to vaginal tissue and thereby promote local intracellular conversion to estrogens, androgens and progesterone so that normal levels of fluid in the vagina is produced. The gel also acts as a moisturizer. An adjustable applicator may also be provided to insure proper placement and dose of the DHEA.

2 Claims, No Drawings

DHEA BIOADHESIVE CONTROLLED RELEASE GEL

CROSS-REFERENCE TO RELATED APPLICATION

This application is a continuation of U.S. patent application Ser. No. 13/696,787, filed on Nov. 7, 2012, now pending, which is a 371 of PCT/US2011/056819, filed Oct. 19, 2011.

FIELD OF THE INVENTION

The present invention relates to medical treatments, and particularly to a DHEA (dehydroepiandrosterone) bioadhesive controlled release gel for controlled and effective delivery of DHEA into vaginal tissue.

DESCRIPTION OF THE RELATED ART

The vaginal wall is comprised of three layers: a squamous epithelium, a lamina propria, a smooth muscle layer and a membrane covering layer. Estrogen functions to keep the epithelium dense, maintain fluid between the layers and the superficial membrane, keeps smooth muscle functional and elastic, and increases the vasodilation in the lamina propria. Estrogen has an effect on the neurotransmitters causing vasodilation.

Androgens and progesterone receptors also play a role in maintaining the integrity of the vaginal wall. Androgens affect epithelial mucification and compactness of the lamina propria's collagen fibers. Muscularis thickness seems to be moderated through an estrogen mechanism and progesterone receptor expression. Androgens are necessary and play a vital role in maintenance of normal vaginal physiology that cannot be achieved with estrogens alone.

Epithelial/endothelial cells and smooth muscle cells of the vagina, vulva, vestibule, labia, and urethra are rich in estrogen and androgen receptors. Therefore, maintenance of the local vaginal tissue is modulated by estrogen, androgens and progesterone.

Factors that influence the health of the vaginal and urogenital tract include: perimenopause, menopause, hysterectomy (partial or total), childbirth, breastfeeding, douching, premature ovarian failure, chemotherapy, and drugs, such as aromatase inhibitors (which decrease estrogen biosynthesis). Tamoxifen may actually increase moisture, but its effect is not enough to overcome estrogen depletion.

The result of the depletion of estrogen, androgens, and progesterone in the vaginal tract causes atrophic vaginitis, vaginal dryness, dyspareunia, itching, burning, irritation, increase in pH, and decreased vaginal flora. These symptoms promote negative sexual health, lack of libido, inability to reach orgasm, and decreased arousal. Vaginal atrophy also increases susceptibility to urinary tract infections. These symptoms can predict poor body image, leading to relationship issues and mental health issues.

Various treatments have been proposed to alleviate or eliminate vaginal dryness. One solution includes a flexible ring inserted into the vagina. The flexible ring releases estrogen into the vaginal tissue for an extended period of time, e.g., three months. However, wearing this ring for extended intervals may be an uncomfortable prospect for some women.

Another solution requires the use of a disposable applicator to insert a tablet containing estrogen into the vagina daily over a period of time. Afterwards, the daily regimen is reduced to periodic reapplication until no longer needed. This treatment may also be uncomfortable by inserting a foreign object into the vagina on a daily or periodic basis.

A still further solution requires the use of a vaginal estrogen cream. An applicator is used to insert the cream into the vagina. This may be a more comfortable solution to the others mentioned above, but the cream can be prone to systemic absorption, which can lead to an increase in serum sex steroids. Such increase is unsuitable for cancer patients and increases the risk of developing cancer.

It has been shown that vaginal estrogen creams, vaginal suppositories and ovules do not resolve all of the vaginal symptoms. Furthermore, the estrogen can be systemically absorbed and raise serum sex steroid levels. If a patient was also taking oral or transdermal estrogen supplementation, the estrogen may reach toxic levels. Vaginal administration of estrogen may interfere in certain cancer treatments where the goal of therapy is to decrease systemic circulating estrogen levels. Vaginal creams can be messy and leak, and some of the dose can be lost. Increased levels of estrogen can actually cause hot flashes. Therefore, vaginal administration of estrogens may actually increase some menopausal symptoms and could increase the risk of breast cancer by increasing systemic levels when not needed Thus, a DHEA bioadhesive controlled release gel solving the aforementioned problems is desired.

SUMMARY OF THE INVENTION

The DHEA bioadhesive controlled release gel includes DHEA mixed in a polymeric gel for the purpose of treating atrophic vaginitis, vaginal dryness, dyspareunia, itching, burning, irritation, increase in pH, and/or decreased vaginal flora. The gel adheres to vaginal tissue and protects the DHEA from systemic absorption, which prevents leakage, loss of DHEA, and elevated levels of systemic DHEA. The gel is configured to slowly erode over time so as to deliver a predetermined dose of DHEA to vaginal tissue and thereby promote local intracellular conversion to estrogens, androgens and progesterone so that normal levels of fluid in the vagina are produced. The gel also acts as a moisturizer. An adjustable applicator may also be provided to insure proper placement and dose of the DHEA.

These and other features of the present invention will become readily apparent upon further review of the following specification.

DETAILED DESCRIPTION OF THE PREFERRED EMBODIMENTS

The DHEA bioadhesive controlled release gel is a mixture of DHEA and polymeric gel for the purpose of treating atrophic vaginitis, vaginal dryness, dyspareunia, itching, burning, irritation, increase in pH, and/or decreased vaginal flora. These symptoms promote negative sexual health, lack of libido, inability to reach orgasm, and decreased arousal. Vaginal atrophy also increases susceptibility to urinary tract infections. These symptoms can predict poor body image, leading to relationship issues and mental health issues. Moreover, the polymeric gel erodes slowly over a period of time to allow for controlled release of the DHEA.

DHEA, or dehydroepiandrosterone, is a natural steroid and hormone precursor that promotes intracellular conversion of various hormones, such as estrogens, androgens and other hormones that maintain normal physiological functions. As mentioned above, menopause and other physiological conditions lower the normal levels of estrogen, resulting in vaginal dryness, among other symptoms mentioned above. When treated with a predetermined dose of DHEA, the DHEA promotes increased production of estrogen so that the normal amount of fluid in the vagina will be produced. Moreover, the treatment promotes vaginal health, which may help reduce the occurrence of cystocele.

In a non-limiting exemplary embodiment, a predetermined amount of micronized DHEA is mixed in a polymeric, bioadhesive gel comprised of carbomer, squalane, vitamin E acetate, water, methylparaben, propylparaben, glycerin, and zinc. The bioadhesive gel exhibits excellent adhesion with the vaginal tissue or the mucous membrane thereof. The gel also performs additional functions. The gel, especially with vitamin E, acts as a vaginal moisturizer that further promotes restoration of normal levels of vaginal fluid. Additionally, the gel surrounds the DHEA so as to protect the same from immediate and systemic absorption in the vaginal environment and leakage of the DHEA.

An important aspect of the gel is the facilitation of time release of the DHEA. Care must be exercised with any type of hormone therapy, since such therapies can have a negative impact on normal hormone levels and other treatments. For example, if an incorrect amount of DHEA is administered, this can potentially increase systemic DHEA levels, which could increase systemic levels of estrogen, androgen, progesterone, and other hormones, creating other physical complications. Moreover, this can compromise other treatments, such as anti-estrogen therapy in cancer patients. To alleviate the above and similar concerns, the gel is configured to erode slowly in the vaginal environment, allowing for controlled and extended release of the DHEA in low doses. The combination of timed or controlled-release and protection increases the efficacy of the DHEA treatment, since this insures that the desired amount of DHEA is introduced into the vaginal tissue. Unlike some of the treatments discussed above, it has been shown that intravaginal administration of DHEA does not increase serum sex steroid levels. The bioadhesive gel, which attaches to the vaginal wall and erodes slowly over time, does not leak, thereby presenting the entire dose to the vaginal environment. By minimizing leaks, the user can administer the DHEA bioadhesive gel with increased convenience and compliance.

The DHEA is taken up by the vaginal tissues and converted through an intracrinological mechanism to estrogen, androgen or progesterone. This avoids needlessly exposing tissues to estrogen when it is not needed. The cells contain all of the enzymes necessary to successfully convert the DHEA to the sex steroid it is lacking.

In the non-limiting exemplary embodiment, the DHEA bioadhesive controlled release gel can be administered by a vaginal applicator. The vaginal applicator can include a type of syringe, e.g., a 1 cc oral syringe, containing a predetermined amount of the gel, e.g., 0.4 ml. The user inserts the applicator barrel up to the 0.8 cc mark on the syringe barrel and depresses the plunger to deliver the gel. It has been found that the 0.8 cc mark is optimal for insuring that the gel is delivered at the proper depth. This procedure can be performed using commercially available 1 cc oral syringe. By simply placing the user's fingers around the desired mark, the fingers can act as an abutment or stop. However, a treatment specific applicator can be provided that includes a 1 cc oral syringe with a circumferentially disposed flange extending from the outer surface of the syringe at the 0.8 mark on the syringe barrel such that the flange functions as a stop or abutment. Due to physiological differences and needs of various individuals, the modified applicator may include features for an adjustable and lockably fixed placement of the circumferential flange. The amount of gel is determined to insure that a sufficient desired dose of DHEA will be thoroughly spread in the vagina.

The following describes an exemplary process for making the DHEA bioadhesive controlled release gel. Various strengths have been found to be effective and the following concerns one containing 3.25 mg of DHEA in 0.4 ml of the DHEA bioadhesive controlled release gel.

EXAMPLE

TABLE 1

List of Materials and Amounts for the Example

| Materials | Amount (in grams) |
|---|---|
| Carbomer 934P NF | 3.0 |
| Squalane NF | 7.0 |
| Vitamin E Acetate USP liquid (1 IU/mg) | 0.05 |
| Water (reverse osmosis) | 83.8555 |
| Methylparaben NF | 0.15 |
| Propylparaben NF | 0.04 |
| Glycerin USP | 5.0 |
| Zinc acetate USP | 0.1 |
| Dehydroepiandrosterone (micronized) | 0.8045 |

Initially, it is to be understood that wherever specific amounts of a substance or material is not mentioned, the amounts thereof are referencing the amounts listed in Table 1. DHEA in the DHEA bioadhesive controlled release gel can be present in an amount of about 0.1-1.0 percent by weight of the bioadhesive controlled release gel. For example, the DHEA bioadhesive controlled release gel can include about 0.8 percent by weight DHEA. Carbomer in the DHEA bioadhesive controlled release gel can be present in an amount of about 3.0 percent by weight of the bioadhesive controlled release gel. Squalane in the DHEA bioadhesive controlled release gel can be present in an amount of about 7.0 percent by weight of the bioadhesive controlled release gel. Vitamin E acetate in the DHEA bioadhesive controlled release gel can be present in an amount of about 0.05 percent by weight of the bioadhesive controlled release gel. Water in the DHEA bioadhesive controlled release gel can be present in an amount of about 83.8 percent by weight of the bioadhesive controlled release gel. Methylparaben in the DHEA bioadhesive controlled release gel can be present in an amount of about 0.15 percent by weight of the bioadhesive controlled release gel. Propylparaben in the DHEA bioadhesive controlled release gel can be present in an amount of about 0.04 percent by weight of the bioadhesive controlled release gel. Glycerin in the DHEA bioadhesive controlled release gel can be present in an amount of about 5.0 percent by weight of the bioadhesive controlled release gel. Zinc acetate in the DHEA bioadhesive controlled release gel can be present in an amount of about 0.1 percent by weight of the bioadhesive controlled release gel. The DHEA bioadhesive controlled release gel can include a mixture having DHEA of a predetermined amount, and a solution having carbomer, squalane, vitamin E acetate, water, methylparaben, propylparaben, glycerin, zinc acetate, and dehydroepiandrosterone, each material having a predetermined amount. The solution can include about 99 percent to about 99.1 percent by weight of the bioadhesive controlled release gel.

The process of preparing the composition began by setting aside the carbomer and a mixture of vitamin E and squalane. 73.8555 g of water was placed in a beaker and heated to 100° C. Methylparaben, propylparaben, and glycerin were added to the heated water and spun until dissolved. Then this solution was set aside to cool. When cool, the solution was placed in an EMP jar capable of holding the total volume to be made.

Ten grams of water was placed in another beaker. Zinc acetate was added to this water and spun until dissolved.

Next, the squalane/vitamin E solution, DHEA and carbomer were placed in another EMP jar and thoroughly mixed for a period of time, e.g., 1 minute. This dispersion was added to the water solution containing methylparaben, propylparaben, and glycerin. The resultant solution was thoroughly mixed for a period of time, e.g., 2 minutes. Then the water/zinc acetate solution was added very slowly and with constant stirring. The whole was finely milled and transferred to another EMP jar. The milled product was mixed at speed for about 0-10 seconds to obtain the DHEA bioadhesive controlled release gel.

The DHEA bioadhesive controlled release gel is a more comfortable and efficient means of counteracting vaginal dryness. The DHEA bioadhesive controlled release gel prevents systemic absorption, since the bioadhesive gel prevents leakage and loss of the DHEA. Moreover, the applicator can be provided as a tailored device suited to the individual so that the correct prescribed amount of the DHEA bioadhesive controlled release gel can be applied at the optimum location. Furthermore, the administration of DHEA in this gel applicator form is a safe means of treating the above-noted symptoms. It is known that oral administration of DHEA may be associated with hirsutism, hair loss, voice changes, stomach distress, and liver function changes. Oral administration may not have a significant positive affect in the local vaginal environment and can increase circulating sex steroid levels, which, in turn, can exacerbate menopausal symptoms and adversely affect disease states and medical treatments.

It is to be understood that the DHEA bioadhesive controlled release gel encompasses a variety of alternatives. For example, the formulation of the gel is not limited to the specific substances or materials noted above. Other materials may be used to manufacture the gel as long as they can erode slowly while allowing efficient delivery of the DHEA.

It is to be understood that the present invention is not limited to the embodiments described above, but encompasses any and all embodiments within the scope of the following claims.

I claim:

1. A method of treating vaginal dryness, dyspareunia, and other symptoms of vagina atrophy in female cancer patients, comprising the steps of:
    selecting a female cancer patient from the group of female cancer patients currently or previously undergoing treatment for breast or other gynecological cancers;
    treating that cancer patient with deoxhydroepiandosterone (DHEA) by administering a bioadhesive controlled release gel having:
        0.3 percent by weight of a carbomer, 7.0 percent by weight of squalane, 0.05 percent by weight of vitamin E acetate, 83.3 percent by weight of water, 0.15 percent by weight of methylparaben, 0.04 percent by weight of propylparaben, 5.0 percent by weight of glycerin, 0.1 percent by weight of zinc acetate, and 0.8 percent by weigh (DHEA);
    whereby upon application, the gel slowly erodes over time to release DHEA into vaginal tissue and treat vaginal dryness, dyspareunia and other symptoms of vaginal atrophy.

2. The method of claim 1, wherein 3.25 mg of DHEA are administered to the female cancer patient.

* * * * *